(12) United States Patent
Nishio et al.

(10) Patent No.: US 7,261,416 B2
(45) Date of Patent: Aug. 28, 2007

(54) EYE'S OPTICAL CHARACTERISTICS MEASURING SYSTEM

(75) Inventors: Kouji Nishio, Itabashi-ku (JP); Gaku Takeuchi, Itabashi-ku (JP); Masahiro Shibutani, Itabashi-ku (JP); Katsuhiko Kobayashi, Itabashi-ku (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 19 days.

(21) Appl. No.: 11/352,730

(22) Filed: Feb. 13, 2006

(65) Prior Publication Data
US 2006/0215112 A1    Sep. 28, 2006

(30) Foreign Application Priority Data
Mar. 23, 2005  (JP) ............... 2005-084269

(51) Int. Cl.
*A61B 3/14*    (2006.01)
*A61B 3/10*    (2006.01)

(52) U.S. Cl. ..................... 351/211; 351/206
(58) Field of Classification Search ......... 351/205–223
See application file for complete search history.

(56) References Cited
U.S. PATENT DOCUMENTS
2003/0156256 A1*  8/2003  Takeuchi et al. ............ 351/205

2006/0146285 A1*  7/2006  Hirohara et al. ............ 351/221

FOREIGN PATENT DOCUMENTS

| JP | 5-56922 | 3/1993 |
|---|---|---|
| JP | 2730880 | 12/1997 |
| JP | 10-43136 | 2/1998 |
| JP | 2002-209852 | 7/2002 |
| JP | 2003-70741 | 3/2003 |

* cited by examiner

*Primary Examiner*—Hung Dang
*Assistant Examiner*—M. Hasan
(74) *Attorney, Agent, or Firm*—Nields & Lemack

(57) ABSTRACT

An eye's optical characteristics measuring system, comprising a target projecting means for projecting a target image on a fundus of an eye under test, a photodetecting means for guiding the target image toward a photoelectric detector, a pupil diameter measuring means, a calculating means for calculating optical characteristics of the eye under test according to distribution of optical intensity obtained based on an image acquired by the photoelectric detector, and an aperture selecting means provided on each of the target projecting means and the photodetecting means, wherein the aperture selecting means is independently driven, and apertures to restrict a projecting luminous flux and a photodetecting luminous flux are selected based on a pupil diameter of the eye under test measured by the pupil diameter measuring means.

9 Claims, 5 Drawing Sheets

EYE'S OPTICAL CHARACTERISTICS MEASURING SYSTEM

BACKGROUND OF THE INVENTION

The present invention relates to an eye's optical characteristics measuring system by which it is possible to measure eye's optical characteristics of an eye under test based on distribution of optical intensity of a target image projected on a fundus of an eye under test.

In the past, an eye's optical characteristics measuring system has been known, which comprises a target projecting means for projecting a target image on a fundus of an eye under test and a photodetecting means for guiding the target image toward a photoelectric detector, and eye's optical characteristics of the eye under test are obtained by calculation based on distribution of optical intensity of the target image detected by the photoelectric detector.

As disclosed in JP-A-2003-70741, an eye's optical characteristics measuring system is proposed, which calculates and display a simulation image on a fundus of an eye, which is formed when a target image is projected on the fundus of an eye under test, from optical characteristics of the eye obtained, and it is possible by this measuring system to objectively find out which kind of image is formed on the fundus of the eye under test and how a subject under test visually perceives the image.

In the eye's optical characteristics measuring system, two or more images of distribution of optical intensity to be measured are acquired, and the optical characteristics of the eye is obtained from one of these images.

In the eye's optical characteristics measuring system as disclosed in JP-A-2003-70741, no consideration is given on a diameter of a luminous flux projected on the eye under test and on a pupil diameter of the eye under test when the image of distribution of optical intensity is acquired. There is individual difference in the pupil diameter of the eye under test, and a diameter of a luminous flux of the light source luminous flux projected to the eye under test is not necessarily adequately suitable for the pupil diameter of the eye under test. Therefore, measurement may not be performed in some cases by using the light source luminous flux adequately suitable for the pupil diameter of the eye under test, and error may occur in the eye's optical characteristics obtained.

SUMMARY OF THE INVENTION

It is an object of the present invention to provide an eye's optical characteristics measuring system, by which it is possible to measure a pupil diameter of an eye under test, to project an adequately suitable light source luminous flux to an eye under test based on the measured pupil diameter and to contribute to the improvement of measuring accuracy and reliability.

To attain the above object, the present invention provides an eye's optical characteristics measuring system, which comprises a target projecting means for projecting a target image on a fundus of an eye under test, a photodetecting means for guiding the target image toward a photoelectric detector, a pupil diameter measuring means, a calculating means for calculating optical characteristics of the eye under test according to distribution of optical intensity obtained based on an image acquired by the photoelectric detector, and an aperture selecting means provided on each of the target projecting means and the photodetecting means, wherein the aperture selecting means is independently driven, and apertures to restrict a projecting luminous flux and a photodetecting luminous flux are selected based on a pupil diameter of the eye under test measured by the pupil diameter measuring means. Also, the present invention provides the eye's optical characteristics measuring system as described above, wherein the pupil diameter measuring means comprises at least the photoelectric detector and the calculating means, and the pupil diameter of the eye under test is calculated by image processing based on an image of an anterior ocular segment of the eye under test as acquired by the photoelectric detector. Further, the present invention provides the eye's optical characteristics measuring system as described above, wherein there is provided an ocular refractive power measuring system to measure refraction degree of the eye under test. Also, the present invention provides the eye's optical characteristics measuring system as described above, wherein the ocular refractive power measuring system comprises a second photoelectric detector to acquire an image of an anterior ocular segment of the eye under test, the pupil diameter measuring means comprises at least the second photoelectric detector and the calculating means, and the pupil diameter of the eye under test is calculated by image processing based on an image of the anterior ocular segment of the eye under test acquired by the second photoelectric detector. Further, the present invention provides the eye's optical characteristics measuring system as described above, wherein an adequate allowable alignment value for an optical axis of the eye under test and a measurement optical axis is set based on the measured pupil diameter of the eye under test, and apertures are selected based on the pupil diameter of the eye under test and on the allowable alignment value. Also, the present invention provides the eye's optical characteristics measuring system as described above, wherein the image acquired by the photoelectric detector includes two or more images at a focusing point and at positions forward and backward of the focusing point to match the refraction degree of the eye under test which is measured by the ocular refractive power measuring system, and an image at an optimal focusing position is selected from the two or more images. Further, the present invention provides the eye's optical characteristics measuring system as described above, wherein the photoelectric detector comprises an assembly of pixels on a photodetection surface, and a position of each pixel on a photodetection surface and configuration of the image on the photodetection surface can be detected based on a photodetection signal. Also, the present invention provides the eye's optical characteristics measuring system as described above, wherein the aperture selecting means comprises an aperture diaphragm where two or more apertures with different diameters are formed and a motor for rotating the aperture diaphragm and for selecting one of the apertures. Further, the present invention provides the eye's optical characteristics measuring system as described above, wherein there is further provided a display unit, a relation between a diameter of a luminous flux restricted by the selected apertures and the pupil diameter of the eye under test is displayed on the display unit, and alignment can be performed by taking the relation between the apertures and the pupil diameter of the eye under test into account.

According to the present invention, an eye's optical characteristics measuring system comprises a target projecting means for projecting a target image on a fundus of an eye under test, a photodetecting means for guiding the target image toward a photoelectric detector, a pupil diameter measuring means, a calculating means for calculating optical characteristics of the eye under test according to distribution of optical intensity obtained based on an image acquired by the photoelectric detector, and an aperture selecting means provided on each of the target projecting means and the photodetecting means, wherein the aperture selecting means is independently driven, and apertures to restrict a projecting luminous flux and a photodetecting luminous flux are selected based on a pupil diameter of the eye under test measured by the pupil diameter measuring means. Accordingly, it is possible to project a projecting luminous flux and a photodetection luminous flux optimal for the pupil diameter of each individual eye under test. Thus, adequate optical characteristics of the eye can be measured without being influenced by individual difference in the pupil of the individual subject under test.

Also, according to the present invention, an adequate allowable alignment value for an optical axis of the eye under test and a measurement optical axis is set based on the measured pupil diameter of the eye under test, and the apertures are selected based on the pupil diameter of the eye under test and on the allowable alignment value. As a result, it is possible to set to an adequate allowable alignment value suitable for the pupil diameter of the eye under test and to the aperture. Thus, the load of the work on the examiner required for alignment can be reduced, and the optical characteristics of the eye can be measured with high efficiency.

Also, according to the present invention, an ocular refractive power measuring system for measuring refraction degree of the eye under test is provided and the image acquired by the photoelectric detector includes two or more images at a focusing point and at positions forward and backward of the focusing point to match the refraction degree of the eye under test which is measured by the ocular refractive power measuring system, and an image at an optimal focusing position is selected from the two or more images. As a result, the examiner has no need to set a target refraction degree, and this contributes to the improvement of working efficiency.

DETAILED DESCRIPTION OF THE PREFERRED EMBODIMENT

Figure 1:
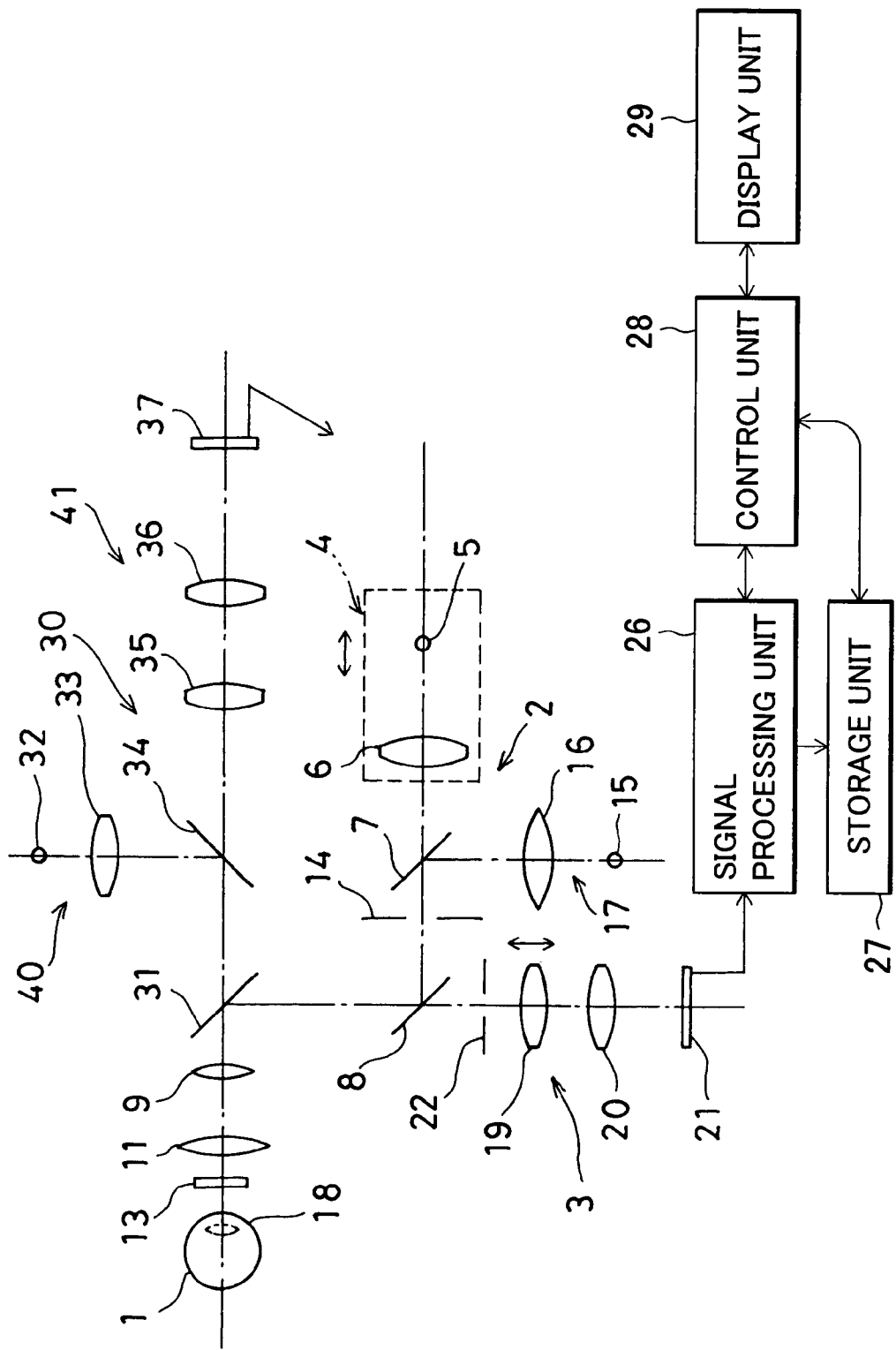
FIG. 1 is a schematical block diagram of an optical system in an embodiment of the present invention.

Description will be given below on the best mode of the invention for carrying out the invention referring to the drawings.

First, referring to FIG. 1, description will be given on an optical system of an eye's optical characteristics measuring system in which the present invention is carried out.

In the figures, reference numeral 1 denotes an eye under test, numeral 2 denotes a projection optical system for projecting a target image to the eye under test 1, 3 denotes a photodetection optical system for guiding the target image obtained from reflection at a fundus of the eye under test 1 toward a photodetector, numeral 4 denotes a light source unit comprising a light source 5 and a relay lens 6, and numeral 30 denotes a system for measuring ocular refractive power. The projection optical system 2, the photodetection optical system 3, and the ocular refractive power measuring system 30 commonly share a portion of an optical axis including the eye under test 1. The projection optical system 2 and the photodetection optical system 3 are separated from the ocular refractive power measuring system 30 by a half-mirror 31. Further, the projection optical system 2 and the photodetection optical system 3 are separated from each other by a polarization beam splitter 8.

The projection optical system 2 comprises the light source 5, the relay lens 6 for converging a projected luminous flux emitted from the light source 5, a half-mirror 7 arranged on an optical axis of the relay lens 6, the polarization beam splitter 8 for directing the projected luminous flux after passing through the half-mirror 7 toward the eye under test 1, and for reflecting and projecting a linearly polarized light compornent (S-linearly polarized light) with a first direction of polarization, a relay lens 9, an objective lens 11, and a ¼ wave plate 13 which are arranged on a projection optical axis of the polarization beam splitter 8 from the side of the polarization beam splitter 8. A projection system aperture diaphragm 14 is arranged at a certain required position on the projection optical system 2, e.g. between the half-mirror 7 and the polarization beam splitter 8. Further, a fixation target system 17 comprising a fixation target 15 and a relay lens 16 is disposed at a position opposite to the half-mirror 7.

The light source 5 and the fixation target 15 are at positions conjugate to a fundus of the eye under test 1. As to be described later, images of the light source 5 and the fixation target 15 are formed on the fundus of the eye under test 1 via a pupil 18. The pupil 18 is at a position conjugate or almost conjugate to the projection system aperture diaphragm 14. On the fixation target 15, a target for optometry, e.g. a Landolt ring, is marked. In the light source unit 4, the light source 5 and the relay lens 6 are integrally disposed, and the light source unit 4 is interlocked with a focusing lens 19 as described later and can be moved in a direction of the optical axis.

The photodetection optical system 3 and the projection optical system 2 commonly share the polarization beam splitter 8 and the relay lens 9, the objective lens 11 and the ¼ wave plate 13 which are arranged on the projection optical axis of the polarization beam splitter 8.

On an reflection optical axis passing through the polarization beam splitter 8, there are provided a photodetection system aperture diaphragm 22, a movable focusing lens 19, and an image forming lens 20 along the reflection optical axis. The image forming lens 20 forms an image of a reflected luminous flux on a photoelectric detector 21. The photoelectric detector 21 is at a position conjugate or almost conjugate to the fundus of the eye under test 1.

Figure 4:
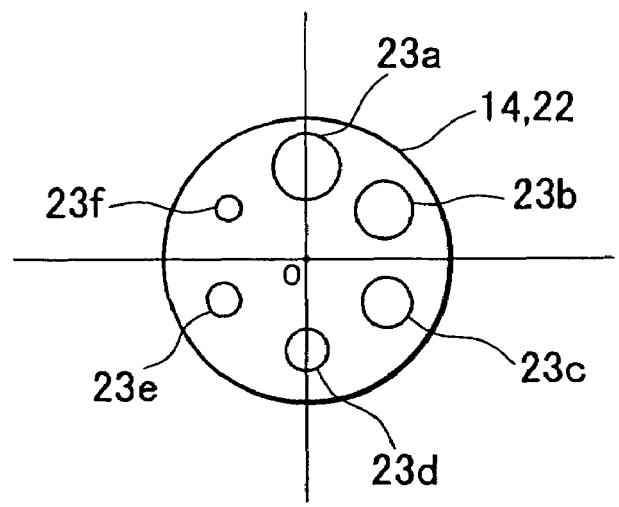
FIG. 4 is a drawing to show an example of an aperture diaphragm of a projection system and a photodetection system used in the embodiment of the present invention.

FIG. 4 shows the projection system aperture diaphragm 14 and the photodetection system aperture diaphragm 22. In the present embodiment, the same component is used as the projection aperture diaphragm 14 and the photodetection system aperture diaphragm 22. Description will be given below on the projection system aperture diaphragm 14.

The projection aperture diaphragm 14 has six apertures 23a, 23b, 23c, 23d, 23e and 23f formed on a disk. The apertures 23a, 23b, 23c, 23d, 23e and 23f are provided at positions by dividing the same circumference to six equal parts. The diameter of each orifice is set to about ∅ 1 mm to ∅ 8 mm by taking the size of the pupil into account. For instance, a diameter of ∅ 1 mm, ∅ 2 mm, ∅ 3 mm, ∅ 4 mm, ∅ 5 mm or ∅ 6 mm is selected.

The projection system aperture diaphragm 14 and the photodetection system aperture diaphragm 22 are designed as rotatable so that the center of each of the apertures 23a, 23b, 23c, 23d, 23e and 23f is aligned with an optical axis of the projection optical system 2 and an optical axis of the photodetection optical system 3. The projection system aperture diaphragm 14 and the photodetection system aperture diaphragm 22 are intermittently rotated at an angle of every 60° by stepping motors (not shown) so that a required one of the apertures 23a, 23b, 23c, 23d, 23e and 23f can be selected. Specifically, a set of the projection system aperture diaphragm 14 and the stepping motor and a set of the photodetection system aperture diaphragm 22 and the stepping motor make up apertures selecting means respectively. Each of the stepping motors is independently controlled by a control unit 28 as described later. It may be designed in such manner that the projection system aperture diaphragm 14 and the photodetection system aperture diaphragm 22 are rotated by a servomotor or the projection system aperture diaphragm 14 and the photodetection system aperture diaphragm 22 may be designed as slidable so that the projection system aperture diaphragm 14 and the photodetection system aperture diaphragm 22 are intermittently and linearly moved by a linear motor or by a stepping cylinder.

The apertures 23a, 23b, 23c, 23d, 23e and 23f are selected to match a diameter of a pupil of an eye of a subject under test. By changing the diameter of the aperture 23 selected at the projection system aperture diaphragm 14 and the diameter of the aperture 23 selected at the photodetection system aperture diaphragm 22, for instance, by setting the diameter of the aperture 23 selected at the photodetection aperture diaphragm 22 smaller than the diameter of the aperture 23 selected at the projection aperture diaphragm 14, it is possible to calculate PTF (Phase Transfer Function) from an image obtained at the photoelectric detector 21.

The photoelectric detector 21 comprises an assembly of pixels on a photodetection surface such as a CCD photodetection sensor. According to a photodetection signal, a position of each pixel on the photodetection surface and configuration and other factors of an image on the photodetection surface can be detected. The position of each pixel and the configuration can be determined by setting coordinates on the photodetection surface and by calculating coordinate value of each pixel.

The photodetection signal from the photoelectric detector 21 is stored in a storage unit 27 via a signal processing unit 26. Writing of data from the signal processing unit 26 to the storage unit 27 is controlled by the control unit 28. As described above, the control unit 28 controls the driving mechanisms and also serves as eye's optical characteristics calculating means. The control unit 28 comprises a simulation image calculating unit and a visual acuity calculating unit and performs calculation as necessary based on the data stored in the storage unit 27, and the results of calculation are displayed on a display unit 29. Various type of programs are stored in the storage unit 27, and these programs include: a sequence program for carrying out measurement, an image processing program for processing image signals from the photoelectric detector 21 and a photoelectric detector 37, a photodetecting image judging program for judging conditions of a photodetecting image based on the signal from the photoelectric detector 21, a calculating program for calculating eye's optical characteristics based on the photodetection signal from the photoelectric detector 21, etc.

Now, description will be given on an ocular refractive power measuring system 30.

The ocular refractive power measuring system 30 measures ocular refractive power of the eye under test 1 and measures the diameter of the pupil of the eye under test 1 based on observation of an anterior ocular segment, and the ocular refractive power measuring system 30 has an arrangement equivalent to an arrangement of a conventional type objective ocular refractive power measuring system.

In the ocular refractive power measuring system 30, reference numeral 40 denotes a target projection optical system for measuring refraction degree by projecting a target image to the fundus of the eye under test 1 to determine the refraction degree. The target projection optical system for measuring refraction degree 40 comprises a target light source 32 and a relay lens 33. A luminous flux of the target image is projected to the fundus of the eye under test 1 via a half-mirror 34 and the half-mirror 31.

Reference numeral 41 denotes a photodetection optical system for measuring refraction degree. A luminous flux, which has been reflected by the fundus of the eye under test 1 and has passes through the half-mirror 31 and the half-mirror 34, is guided toward the photoelectric detector 37 via a relay lens 35 and an image forming lens 36. The photoelectric detector 37 can also take an image of the anterior ocular segment of the eye under test 1 so that an image of the anterior ocular segment can be obtained during the measurement of ocular refractive power or when eye's optical characteristics are measured.

A photodetection signal of an image obtained at the photoelectric detector 37 is outputted to the control unit 28, and the diameter of the pupil of the eye under test is calculated by necessary means such as image processing. The photodetecting intensity is different between a photodetecting luminous flux from a portion of the pupil and a luminous flux from a portion of an iris in the surrounding region. In the image processing for calculating the pupil diameter, for instance, a position of a boundary between the pupil and the iris is determined from the distribution of optical intensity on a line to traverse the pupil, and the pupil diameter is calculated from the position of the boundary thus determined.

Based on the diameter of the pupil of the eye under test thus calculated, optimal apertures are selected from the apertures 23a, 23b, 23c, 23d, 23e and 23f.

Figure 2:
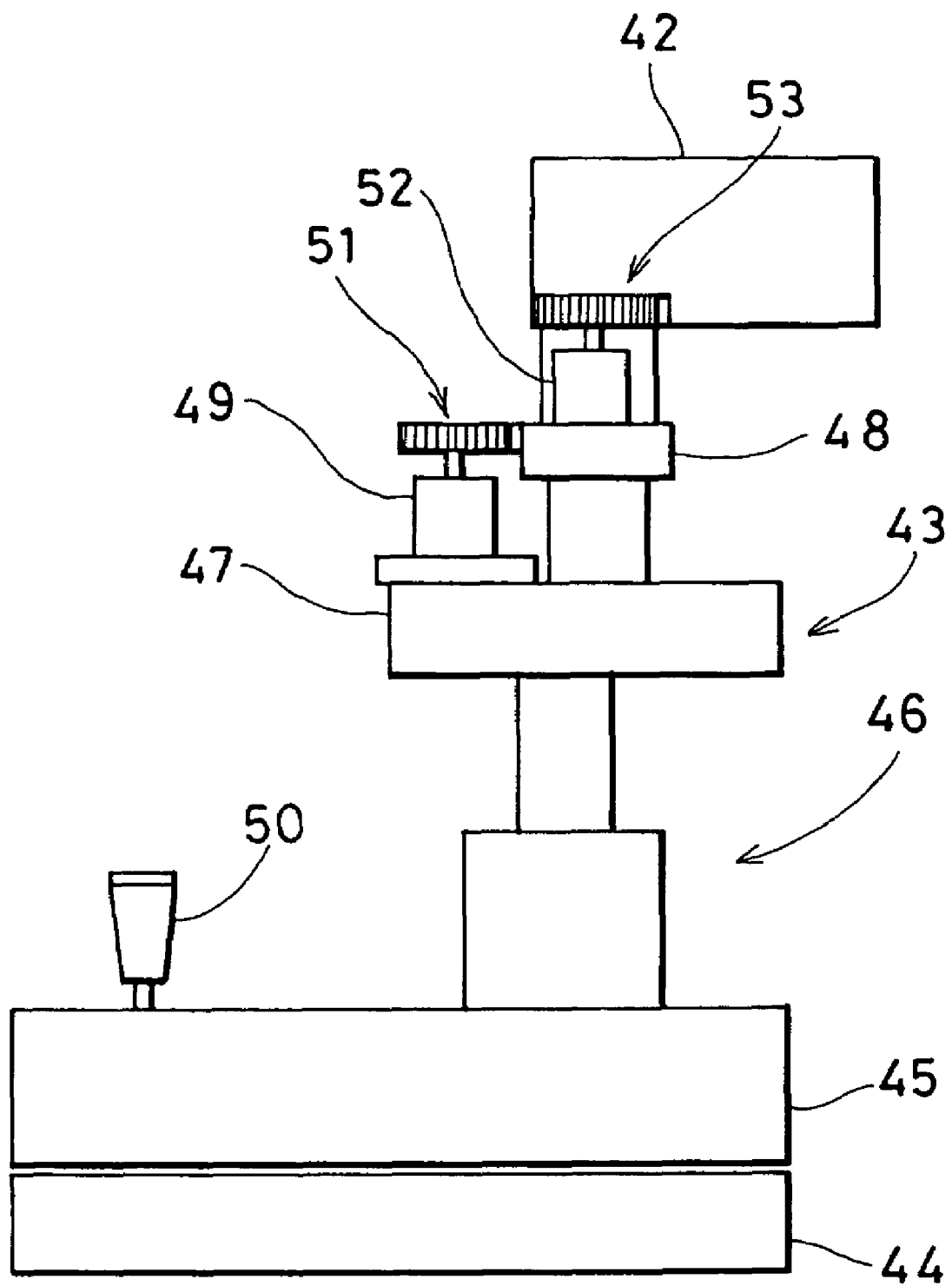
FIG. 2 is a schematical side view of an alignment mechanism used in the embodiment of the present invention.
Figure 3:
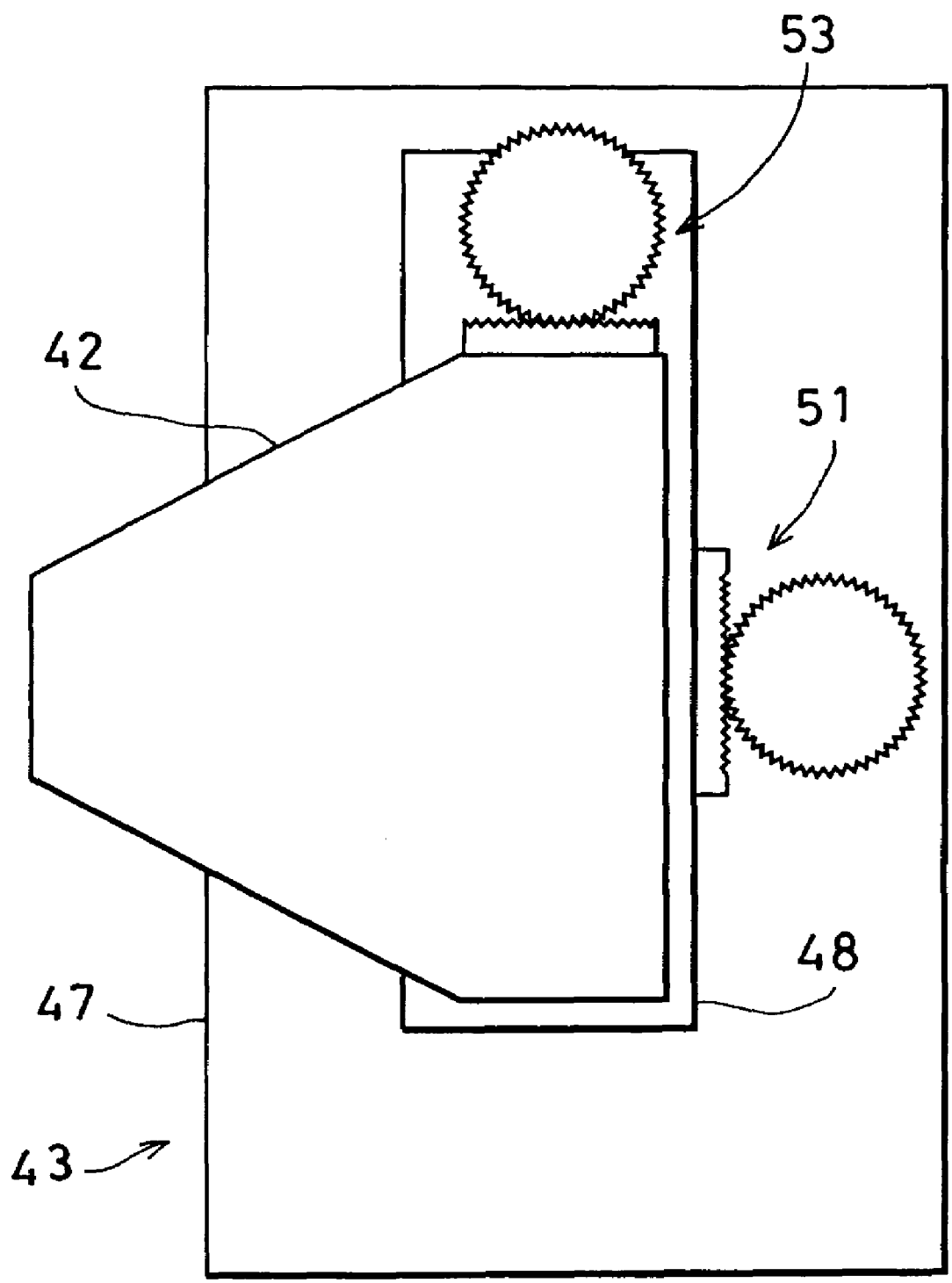
FIG. 3 is a schematical plan view of the alignment mechanism used in the embodiment of the present invention.

As shown in FIG. 2 and FIG. 3, the eye's optical characteristics measuring system comprises an alignment mechanism, which aligns an optical axis of the eye's optical characteristics measuring system with an optical axis of the eye under test.

In FIG. 2 and FIG. 3, reference numeral 42 represents a measuring unit where the optical system as described above is accommodated. The measuring unit 42 is supported by an alignment mechanism 43 in such manner that the measuring unit 42 can be moved upward, downward, forward, backward, leftward or rightward.

A sliding table 45 is installed on a base 44 so that the sliding table 45 can be moved forward, backward, leftward or rightward. The sliding table 45 can be moved forward, backward, leftward, or rightward by operating a control lever 50. An examiner can perform rough adjustment for alignment by operating the control lever 50.

On the sliding table 45, a lifting table 47 is installed via a lift driving unit 46 so that the lifting table 47 can be moved upward or downward. On the lifting table 47, a left-right sliding table 48 is installed so that the left-right sliding table 48 can be moved leftward or rightward. The left-right sliding table 48 is driven by a left-right adjusting motor 49 mounted on the lifting table 47 via a rack pinion mechanism 51. On the left-right sliding table 48, the measuring unit 42 is mounted so that the measuring unit 42 can be moved forward or backward. The measuring unit 42 is driven by a front-back adjusting motor 52 installed on the left-right sliding table 48 via a rack pinion mechanism 53.

In the alignment process, an image of the anterior ocular segment is taken. Based on the image of the anterior ocular segment thus taken, the control unit 28 calculates a difference between an optical axis of the eye under test and a measuring optical axis of the eye's optical characteristics measuring system. Based on the results of calculation, the lift driving unit 46, the left-right adjusting motor 49, and the front-back adjusting motor 52 are controlled, and alignment can be automatically performed.

Next, description will be given on operation of the above optical system.

With the eye under test 1 gazing at the fixation target 15, a projecting luminous flux is projected by the projection optical system 2. A visible light is used for the fixation target 15, and an infrared light is used for the projecting luminous flux.

Then, refraction degree of the eye under test 1 is measured by the ocular refractive power measuring system 30, and a diameter of the pupil of the eye under test are measured. Based on the measurement result, the control unit 28 controls the stepping motors (not shown) and rotates the projection system aperture diaphragm 14 and the photodetection aperture diaphragm 22, and optimal apertures are selected from the apertures 23a, 23b, 23c, 23d, 23e and 23f.

Figure 5A:
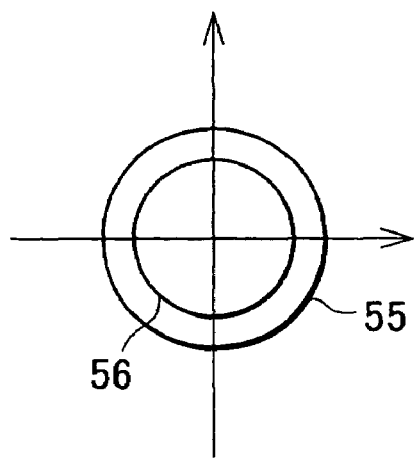
FIG. 5 (A), FIG. 5 (B) and FIG. 5 (C) each represents a drawing to show alignment condition of diameter of luminous flux and pupil diameter of the eye under test in the embodiment of the present invention.
Figure 5B:
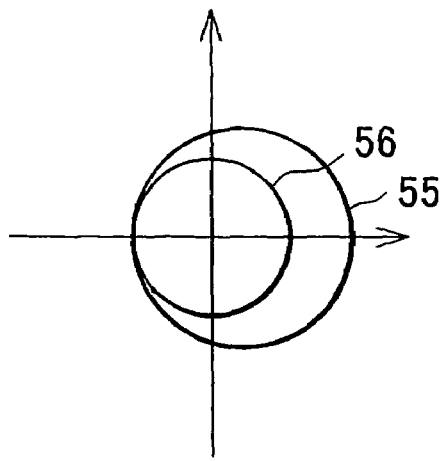
Figure 5C:
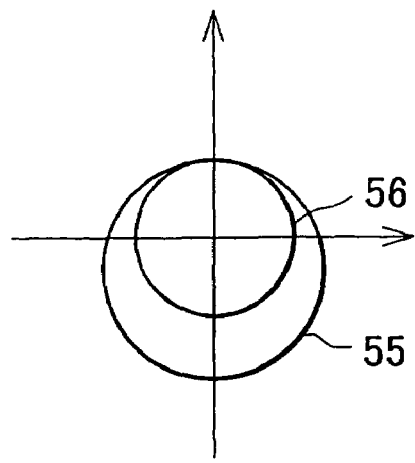

When the apertures 23 are selected, an allowable alignment value is set based on the relation between the pupil diameter of the eye under test and the selected aperture 23. FIG. 5 (A) to FIG. 5 (C) each represents the relation between a luminous flux diameter 55 restricted by the selected aperture 23 and a pupil diameter 56 of the eye under test. For example, it is supposed that the pupil diameter is ⌀ 4.5 mm and that the restricted luminous flux diameter is ⌀ 5 mm. Because the pupil diameter 56 of the eye under test should not be larger than the luminous flux diameter 55, the allowable alignment value is ±0.25 mm in two directions crossing perpendicularly each other. As the allowable alignment value, a value to match the pupil diameter 56 of the eye under test is set, and the aperture 23 is selected according to the pupil diameter 56 of the eye under test and to the allowable alignment value thus set.

The relation between the luminous flux diameter 55 and the pupil diameter 56 of the eye under test as shown in FIG. 5 (A) to FIG. 5 (C) is displayed on the display unit 29. By giving consideration on the relation between the luminous flux diameter 55 and the pupil diameter 56 of the eye under test as displayed on the display unit 29, an examiner aligns the optical axis of the eye under test with the optical axis of the eye's optical characteristics measuring system, and the measurement is started when the pupil diameter 56 of the eye under test falls within the luminous flux diameter 55.

A projected luminous flux (infrared light) emitted from the light source 5 passes through the relay lens 6 and the half-mirror 7. The transmitted projected luminous flux has its luminous flux diameter 55 restricted by the aperture diaphragm 14, and the projected luminous flux reaches the polarization beam splitter 8. An S-linearly polarized light component is reflected by the polarization beam splitter 8, and the S-linearly polarized light component passes through the relay lens 9. Then, the S-linearly polarized light component is projected to the fundus of the eye under test 1 by the objective lens 11 via the ¼ wave plate 13, and a primary target image is formed as a point image.

After passing though the ¼ wave plate 13, the S-linearly polarized light is turned to a right circularly polarized light. The projected luminous flux is reflected by the fundus of the eye under test 1. When reflected by the fundus, the reflected luminous flux is turned to a left circularly polarized light. Further, when the reflected luminous flux passes through the ¼ wave plate 13, the reflected luminous flux is turned to a P-linearly polarized light, which has a direction of polarization by 90° different from a direction of polarization of the S-linearly polarized light.

The P-linearly polarized light is guided toward the polarization beam splitter 8 via the objective lens 11 and the relay lens 9. The polarization beam splitter 8 reflects the S-linearly polarized light and allows the P-linearly polarized light to pass. Thus, the reflected luminous flux passes through the polarization beam splitter 8, and the diameter of the receiving luminous flux is determined by the photodetection system aperture diaphragm 22. After passing though the photodetection system aperture diaphragm 22, the reflected luminous flux is formed as a secondary target image on the photoelectric detector 21 by the focusing lens 19 and the image forming lens 20.

The distribution of optical intensity of the secondary target image received by the photoelectric detector 21 reflects optical characteristics of the eye under test 1. By detecting the photodetecting condition of the photoelectric detector 21, the optical characteristics of the eye can be measured.

Figure 6:
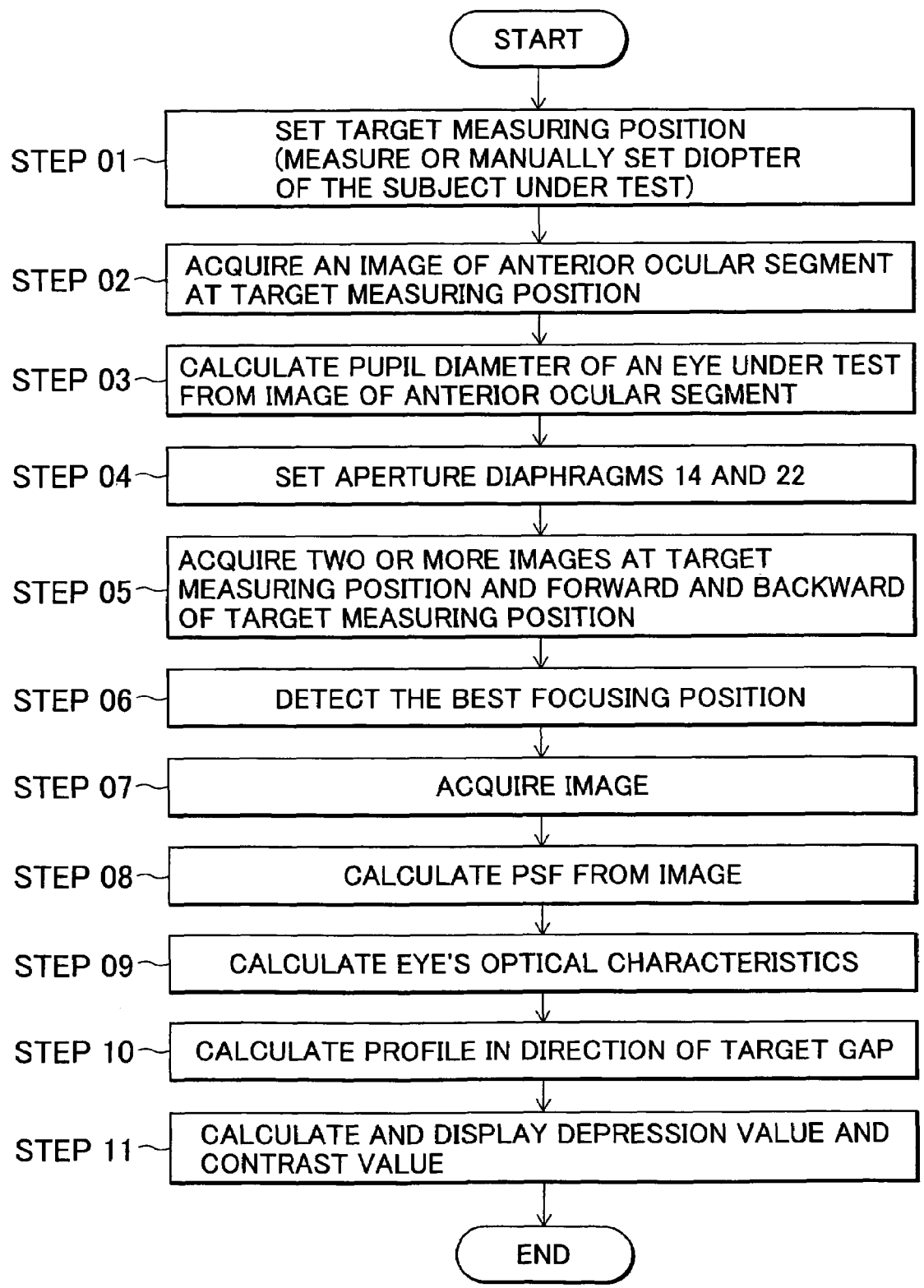
FIG. 6 is a flow chart to explain measurement of optical characteristics of an eye.

Referring to FIG. 6, description will be given now on the flow of the measurement of optical characteristics of the eye.

[Step 01] Refraction degree of the eye under test 1 of the subject under test is measured by the ocular refractive power measuring system 30. The refraction degree thus measured is inputted to the control unit 28, and a target measuring position (position in a direction toward depth of focus to be taken) is set. The target measuring position may be manually set based on the measurement result of the ocular refractive power measuring system 30.

[Step 02] An image of the anterior ocular segment of the subject under test at the target measuring position is acquired by the ocular refractive power measuring system 30.

[Step 03] From the image of the anterior ocular segment, the pupil diameter of the eye under test 1 is calculated by image processing.

[Step 04] From the pupil diameter of the eye under test thus calculated, the allowable alignment value is calculated. From the pupil diameter of the eye under test and the allowable alignment value, the aperture 23 at the projection system aperture diaphragm 14 and the aperture 23 at the photodetection system aperture diaphragm 22 are determined. By controlling the stepping motors (not shown), the projection system aperture diaphragm 14 and the photodetection system aperture diaphragm 22 are rotated, and the apertures 23 as required are selected.

[Step 05] A measuring luminous flux is projected to the eye under test 1 via the projection optical system 2 from the light source 5. The light source unit 4 and the focusing lens 19 are moved together by interlocking. The light source unit 4 and the focusing lens 19 are moved at two or more positions forward and backward including the target measuring position, e.g. at a step of 0.03 D. For the target image on each step, two or more images are acquired according to the photodetection signal from the photoelectric detector 21.

[Step 06] From the plurality of images thus acquired, condition of the focus point is determined according to the configuration of the image, and the best focusing position of the target image received is obtained. Among the images from the photoelectric detector 21, images having a predetermined brightness or higher are selected. Further, for the configurations of the images exceeding a predetermined slice level, the size in two directions crossing perpendicularly is calculated. The image, which has approximately the same size in two directions perpendicularly crossing, is judged as an image at the best focusing position.

[Step 07] The image at the best focusing position is selected as an image for calculating the optical characteristics of the eye.

[Step 08 and Step 09] On the selected image, optical characteristics of the eye such as PSF are calculated.

[Step 10] A profile in a direction of target gap is calculated.

[Step 11] Further, a depression value and a contrast value are calculated. The depression value and the contrast value thus calculated are displayed on the display unit 29.

On the calculation of the optical characteristics of the eye such as PSF, the profile in the direction of target gap, and the depression value and the contrast value as described in Step 08 to Step 11, description is given in the Japanese Patent Application 2000-364834 (JP-A-2002-209852).

In the above embodiment, the image of the anterior ocular segment to measure the pupil diameter of the eye under test is picked up by the ocular refractive power measuring system 30, while the image may be picked up by the photodetection optical system 2 and the photodetection optical system 3. The light source unit 4 and the focusing lens 19 are regarded to be at the positions of the preset refraction degree. Under this condition, the light source 5 is turned on to illuminate the anterior ocular segment. An image of the anterior ocular segment is acquired by the photoelectric detector 21. The acquired image is processed by image processing, and the pupil diameter of the eye under test 1 is calculated.

According to the present invention, the pupil diameter of the eye under test is measured, and an adequate projecting luminous flux is set. Further, the optimal allowable alignment value is set. The image to calculate the optical characteristics of the eye is acquired under the optimal condition. Therefore, the optical characteristics of the eye can be measured without impairing measurement accuracy when measurement is made on the eye under test with any pupil diameter. Also, operability of alignment is not impaired, and this contributes to the execution of measuring operation with high efficiency.

What we claim is:

1. An eye's optical characteristics measuring system, comprising a target projecting means for projecting a target image on a fundus of an eye under test, a photodetecting means for guiding the target image toward a photoelectric detector, a pupil diameter measuring means, a calculating means for calculating optical characteristics of the eye under test according to distribution of optical intensity obtained based on an image acquired by the photoelectric detector, and an aperture selecting means provided on each of said target projecting means and said photodetecting means, wherein said aperture selecting means is independently driven, and apertures to restrict a projecting luminous flux and a photodetecting luminous flux are selected based on a pupil diameter of the eye under test measured by said pupil diameter measuring means.

2. An eye's optical characteristics measuring system according to claim 1, wherein said pupil diameter measuring means comprises at least said photoelectric detector and said calculating means, and the pupil diameter of the eye under test is calculated by image processing based on an image of an anterior ocular segment of the eye under test which is acquired by said photoelectric detector.

3. An eye's optical characteristics measuring system according to claim 1, wherein there is provided an ocular refractive power measuring system to measure refraction degree of the eye under test.

4. An eye's optical characteristics measuring system according to claim 3, wherein said ocular refractive power measuring system comprises a second photoelectric detector to acquire an image of an anterior ocular segment of the eye under test, said pupil diameter measuring means comprises at least said second photoelectric detector and said calculating means, and the pupil diameter of the eye under test is calculated by image processing based on an image of the anterior ocular segment of the eye under test acquired by said second photoelectric detector.

5. An eye's optical characteristics measuring system according to claim 2 or 4, wherein an adequate allowable alignment value for an optical axis of the eye under test and a measurement optical axis is set based on the measured pupil diameter of the eye under test, and the apertures are selected based on the pupil diameter of the eye under test and on the allowable alignment value.

6. An eye's optical characteristics measuring system according to claim 3, wherein the image acquired by said photoelectric detector includes two or more images at a focusing point and at positions forward and backward of the focusing point to match the refraction degree of the eye under test which is measured by said ocular refractive power measuring system, and an image at an optimal focusing position is selected from said two or more of images.

7. An eye's optical characteristics measuring system according to claim 1, wherein said photoelectric detector comprises an assembly of pixels on a photodetection surface, and a position of each pixel on a photodetection surface and configuration of the image on the photodetection surface can be detected based on a photodetection signal.

8. An eye's optical characteristics measuring system according to claim 1, wherein said aperture selecting means comprises an aperture diaphragm where two or more apertures with different diameters are formed and a motor for rotating said aperture diaphragm and for selecting one of said apertures.

9. An eye's optical characteristics measuring system according to claim 5, wherein there is further provided a display unit, a relation between a diameter of a luminous flux restricted by said selected aperture and the pupil diameter of the eye under test is displayed on said display unit, and alignment can be performed by taking said relation between said apertures and the pupil diameter of the eye under test into account.

* * * * *